United States Patent [19]

Wolfe

[11] Patent Number: 5,229,137
[45] Date of Patent: Jul. 20, 1993

[54] METHODS AND PHARMACEUTICAL COMPOSITIONS FOR TREATING EPISODIC HEARTBURN

[75] Inventor: M. Michael Wolfe, Newton, Mass.

[73] Assignee: Brigham and Women's Hospital, Inc., Boston, Mass.

[21] Appl. No.: 879,662

[22] Filed: May 6, 1992

[51] Int. Cl.$^5$ .............. A61K 33/10; A61K 33/08; A61K 33/00; A61K 31/695; A61K 31/425; A61K 31/415; A61K 31/34

[52] U.S. Cl. .............. 424/687; 424/690; 424/692; 424/717; 514/63; 514/365; 514/370; 514/400; 514/461; 514/819; 514/820

[58] Field of Search .............. 424/688, 687, 682, 690, 424/692, 717; 514/400, 461, 820, 63, 365, 370, 819

[56] References Cited

U.S. PATENT DOCUMENTS

| | | | |
|---|---|---|---|
| 4,127,650 | 11/1978 | Buehler | 424/687 |
| 4,316,888 | 2/1982 | Nelson | 424/127 |
| 4,676,984 | 6/1987 | Wu et al. | 424/157 |
| 4,684,632 | 8/1987 | Schultz | 514/78 |
| 4,689,229 | 8/1987 | Banik | 424/195.1 |
| 4,704,278 | 11/1987 | Wu et al. | 424/157 |
| 4,705,683 | 11/1987 | Dettmar | 514/400 |
| 4,846,836 | 7/1989 | Reich | 623/11 |
| 4,857,324 | 8/1989 | Mir et al. | 424/690 |
| 4,861,592 | 8/1989 | Gottwald et al. | 424/687 |
| 4,918,063 | 4/1990 | Lichtenberger | 514/78 |
| 4,950,656 | 8/1990 | Lichtenberger | 514/78 |

OTHER PUBLICATIONS

Avery's Drug Treatment, 3rd edition (1987) pp. 742–743.
Steinberg, W. M. et al.: *N Engl J Med*, 307(7):400–404 (Aug. 12, 1982).
Mihaly, G. W. et al.: *Br Med J*, 285:998–999 (Oct. 9, 1982).
Harvey, Stewart C., "Chapter 42: Gastric Antacids, Miscellaneous Drugs for the Treatment of Peptic Ulcers, Digestions, and Bileacids" *Goodman & Gilman's The Pharmacological Basis of Therapeutics*, 7th Ed., McMillan (1985).
Douglas, W., "Chaper 26: Histamine and 5-Hydroxy--Tryptamine (Serotonin) and Their Antagonists," *Goodman & Gilman's The Pharmacological Basis of Therapeutics*, 7th Ed., McMillan Publishing (1985).
O'Laughlin et al.: "Healing of Aspirin-Associated Peptic Ulcer Disease Despite Continued Colicilate Injection", *Archives of Internal Medicine*, 141:781–783 (1981).

(List continued on next page.)

Primary Examiner—Frederick E. Waddell
Assistant Examiner—Raymond J. Henley, III
Attorney, Agent, or Firm—Ruden, Barnett, McClosky, Smith, Schuster & Russell

[57] ABSTRACT

Pharmaceutical medications and methods are disclosed for providing instant and sustained relief from pain or symptoms associated with episodic heartburn in humans. The medications consist essentially of antacids and histamine $H_2$-receptor antagonists, and may be administered on an as-needed basis in liquid or solid dosage forms. Typical antacids which may be used in combination with the histamine $H_2$-receptor antagonist are conventional antacids which are well known and widely used in the treatment of excess acid related gastrointestinal dysfunctions. Exemplary of typical antacids include, sodium bicarbonate, calcium carbonate, magnesium hydroxide and aluminum hydroxide, as well as commercially available high potency, flavored antacids. Histamine $H_2$-receptor antagonists which may be used in combination include those conventionally used in the treatment of peptic ulcers, such as, for example, cimetidine, ranitidine, famotidine and nizatidine. In carrying out the methods, an antacid and histamine $H_2$-receptor antagonist may be administered together as a single unitary dose in the form of a liquid or solid, or administered together, but separately as either liquids or solids or a combination thereof. The oral medications when formulated as a single unitary dose may include other additives, such as, for example, antiflatulents, flavorings, sweeteners and the like.

27 Claims, No Drawings

OTHER PUBLICATIONS

Weserstein, M. et al.: "In Vivo Evaluation of the Effect of Antacids and H₂ Blockers and Intragastric pH in the Gastric and Duodeanl Ulser," *Acta Gastroenterol. Latinoam*, 15(4):243-256 (1985).

Histamine H₂-Receptor Antagonists Systemic, *USP DI Review Page*, 1-24 (Jun. 17, 1992).

Frislid, K. et al.: *Br Med J*, 286:1358 (1983).

S. van Avermaet et al.: *Gastroenterology*, 102 (4) Part II, A184 Abstracts (1992).

*Drug Evaluation Monographs*, Micromedex, Inc. 76 Exp. (May 31, 1993).

*Drug Evaluation Monographs*, Micromedex, Inc.,· 76 Exp. (May 31, 1993).

*Drug Consults*, Micromedex, Inc., 76 Exp. (May 31, 1993).

*Drug Interaction Facts*, Facts and Comparisons, 338 (Apr., 1991).

*Drug Interaction Facts*, Facts and Comparisons, 187 (Jul., 1991).

Lin, H. F.: *Clin. Pharmacokinet.*, 20(3):218-236 (1991).

Desager, J. P. et al.: *J. International Medical Research*, 17:62-67 (1989).

*Drug Interaction Facts*, Facts and Comparisons, 612 (Jul., 1990).

Stockley, I. H.: *Drug Ineractions, A Source Book of Adverse Interactions, Their Mechanisms, Clinical Importance and Management*, 2nd Ed., Blackwell Scientific Publicaitons 614-615 (1991).

Shelly, D. W. et al.: *Drug Intell. Clin. Pharm.*, 20:792-795 (Oct., 1986).

Albin, H. et al.: *Eur. J. Clin. Pharmacol.*, 32:97-99 (1987).

D'Arcy, P. F. et al.: *Drug Intell. Clin. Pharm.*, 21:607-617 (1987).

Donn, K. H. et al.: *Pharmacotherapy*, 4:89-92 (1984).

Hansten, P. D. et al.: *Drugs Interactions Newsletter*, 5(3):11-14 (Mar., 1985).

Gannoulis, N. et al.: *Gastroenterology*, 90:A1393 (May, 1986).

Albin, H. et al.: *Eur. J. Clin. Pharmacol.*, 26:271-273 (1984).

Russell, W. L. et al.: *Digestive Diseases and Sciences*, 29(5):385-389 (May, 1984).

Mahachai, V. et al.: *Clinical Therapeutics*, 6(6):808-823 (1984).

Steinberg, W. M. et al.: *Gastroenterology*, 78:A1269 (May, 1980).

Gugler, R. et al.: *Eur. J. Clin. Pharmacol.*, 20:225-228 (1981).

Gugler, R. et al.: *Clin. Pharmacol. Ther.*, 29(6):744-748 (Jun., 1981).

Bodemar, G. et al.: *Br. Soc. Gastroenterology*, 19:A990 (1979).

Bodemar, G. et al.: *Lancet* (Letter), 444-445 (Feb. 24, 1979).

Ganjian, F. et al.: *J. Pharm. Sci.*, 69(3):352-353 (Mar., 1980).

Burland, W. L. et al.: *Lancet*, (Letter) 965 (Oct. 30, 1976).

Longstreth, G. F. et al.: *Gastroenterology*, 72(1):9-13 (1977).

Clayman, C. B.: *JAMA*, 238(12):1289-1290 (Sep. 19, 1977).

Lin, J. H. et al.: *Br. J. Clin. Pharmac.*, 24:551-553 (1987).

Gallaghan, J. T. et al.: *Scanned J. Gastroenterol.*, 22(Suppl 136):9-17 (1987).

Barzaghi, N. et al.: *Eur. J. Clin. Pharmacol.*, 37:409-410 (1989).

METHODS AND PHARMACEUTICAL COMPOSITIONS FOR TREATING EPISODIC HEARTBURN

FIELD OF THE INVENTION

The present invention relates to pharmaceutical compositions and methods for providing immediate and sustained relief from pain, discomfort and/or symptoms associated with episodic heartburn in humans.

BACKGROUND

About 7-10 percent of all people suffer daily, and about 25-40 percent monthly, from pain, discomfort and/or symptoms associated with episodic heartburn. Episodic heartburn is defined as the sensation of burning under the sternum (breastbone) and is usually associated with the ingestion of different foods. Episodic heartburn has also been referred to as "sour stomach," "indigestion," and "waterbrash/regurgitation." Although different foods, such as coffee, mints, fatty foods, alcohol, and chocolate, are usually implicated in the etiology of episodic heartburn, these symptoms can be caused by any type of food in certain people. Moreover, in many people, there is no inciting agent that can be identified, rather the disorder occurs without any known provocation.

At present, the primary treatment is based upon the neutralization of gastric acid and pepsin with antacids, such as, for example, aluminum hydroxides, calcium carbonates, magnesium hydroxides and sodium bicarbonates. Of less importance, treatment is based upon the inhibition of secretion by histamine $H_2$-receptor antagonists, such as cimetidine and ranitidine.

Unfortunately, both of these treatments have proven to be inadequate. The problem with antacids is that they provide only transient relief. This disadvantage is emphasized in many people at night where symptomatic relief is not provided. The problem with histamine $H_2$-receptor antagonists is that relief is typically not experienced until about forty minutes to about two hours after the medication is ingested. Moreover, the simultaneous administration of antacids and histamine $H_2$-receptor antagonists have been discouraged based upon studies demonstrating that antacids decrease absorption and subsequent blood levels of histamine $H_2$-receptor antagonists, such as cimetidine and ranitidine. See, for example, Steinberg, W. et al.: *N. Engl. J. Med.*, 307:400-404 (1982), and Frislid, K. et al.: *Br. Med. J.*, 286:1358 (1983); and Mihaly, G. W. et al.: *Br. Med J.*, 285(6347):998-9 (Oct. 9, 1982).

Consequently, there is a need for a treatment which can effectively provide both instant and sustained relief from pain, discomfort and/or symptoms associated with episodic heartburn in humans.

SUMMARY OF THE INVENTION

In brief, the present invention alleviates and overcomes certain of the above-mentioned drawbacks and shortcomings through the discovery of novel pharmaceutical medications and methods for providing immediate, temporary and sustained relief to people who suffer from episodic heartburn. Generally speaking, the pharmaceutical medications include an effective amount of an antacid and a histamine $H_2$-receptor antagonist, and the methods involve administering together or substantially together an antacid and a histamine $H_2$-receptor antagonist at or after the onset of pain, discomfort and/or symptoms caused by episodic heartburn. The present invention is based upon the unexpected realization that antacids and histamine $H_2$-receptor antagonists can be effectively administered together or substantially together to achieve continuous relief from pain, discomfort and/or symptoms associated with episodic heartburn, notwithstanding current medical teachings against the simultaneous administration of antacids and histamine $H_2$-receptor antagonists.

The novel pharmaceutical medications of the instant invention are formulated so that they can be administered orally on an as needed basis to obtain the symptomatic relief. In other words, it is not necessary to take the novel pharmaceutical medications or practice the methods of the present invention on a regimented schedule to obtain effective relief. Rather, the medications can be taken and the methods of the present invention can be practiced by people whenever needed, that is, at the onset of pain, discomfort or symptoms, or whenever pain, discomfort or symptoms are experienced. In accordance with the present invention, this is simply accomplished by orally ingesting together or at basically the same time, an effective amount of an antacid and an $H_2$-receptor antagonist whenever an attack of episodic heartburn has surfaced.

The above features and advantages of the present invention will be better understood with reference to the following Detailed Description and Examples which are illustrative of the present invention.

DETAILED DESCRIPTION OF THE INVENTION

By way of illustrating and providing a more complete appreciation of the present invention and many of the intendant advantages thereof, the following Detailed Description is given concerning the novel pharmaceutical medications and methods for providing people suffering from episodic heartburn with instant and sustained relief.

As set forth in the Background, by the term "episodic heartburn," it is meant herein to refer to the sensation of burning under the sternum (breastbone) usually, but not necessarily, associated with the ingestion of different foods. Also included in this definition of "episodic heartburn" is sour stomach, indigestion and waterbrash/regurgitation.

By the term "histamine $H_2$-receptor antagonist(s)," it is referred to herein in a broad sense and is meant to include those agents that inhibit or block the secretion of gastric acid by binding to a specific histamine receptor on the parietal (acid-secreting) cell membrane located in the stomach. Exemplary of histamine $H_2$-receptor antagonists contemplated by the present invention are cimetidine, ranitidine, nizatidine and famotidine.

By the term "antacid(s)," it too is used broadly herein and refers to those agents which can block gastric acid and/or bile salts by neutralization, and/or inhibit the proteolytic activity of pepsin. Antacids which may be used in combination with the histamine $H_2$-receptor antagonists in the present invention are conventional antacids which are well known and widely used in the treatment of a variety of excess acid-related gastrointestinal dysfunctions including acid indigestion, heartburn, sour stomach and ulcers. Typical antacids contemplated by the present invention include, for example, aluminum hydroxides, calcium carbonates, magnesium hydroxides, sodium bicarbonates and the like, as well as those antacids that are commercially available. In accordance with the present inventions, the antacids may be used in dosage amounts conventionally used for treatment of a variety of excess acid-related gastrointestional dysfunctions, as discussed above.

By the terms "immediate, temporary and sustained relief," they too are used in a broad sense herein. More particularly, the term "immediate relief" means that relief obtained from pain, discomfort and/or symptoms associated with episodic heartburn which occurs within about 5-10 minutes following ingestion of the active ingredients or an antacid. "Temporary relief" on the other hand refers to relief from pain, discomfort and/or symptoms associated with episodic heartburn which lasts in duration on the order of between about 30 minutes and 90 minutes after ingestion of the active ingredients or an antacid. With respect to "sustained relief," it refers to relief obtained from pain, discomfort and/or symptoms associated with episodic heartburn which lasts in duration for over about 4-6 hours following ingestion of the active ingredients or the histamine $H_2$-receptor antagonists. It should therefore be appreciated that by the term "immediate and sustained relief," it means herein immediate, temporary and sustained relief which starts within about 5-10 minutes following ingestion of the active ingredients and continues and remains constant for at least about 4-6 hours after ingestion of the active ingredients; the actual ingredients being an antacid and a histamine $H_2$-receptor antagonist.

The pharmaceutical medications of the instant invention can be conveniently prepared from, for example, commercially available antacids and histamine $H_2$-receptor antagonists and may be formulated into liquid or solid dosage forms or combinations thereof. For example, the pharmaceutical medications may be taken as a single unitary dose containing both the antacid and the histamine $H_2$-receptor antagonist in a liquid or solid dosage form. Likewise, the present invention contemplates taking the ingredients substantially together, but separately in the same or different dosage forms, such as taking the antacid as a liquid dose and the histamine $H_2$-receptor antagonist as a solid dose or vice versa, or taking them both separately as either solid or liquid doses.

When taking the active ingredients substantially together, but separately in same or different dosage forms, the order in which they are ingested is not critical. In other words, the antacid and the histamine $H_2$-receptor antagonist may be ingested simultaneously, or the antacid may be ingested first followed by the histamine $H_2$-receptor antagonist, or the $H_2$-receptor antagonist may be first ingested followed by the antacid. It is preferable, however, to formulate the antacids and the histamine $H_2$-receptor antagonists into single liquid mixtures which can be co-ingested as single unitary dosages on an as-needed basis, i.e., at or after the onset of pain, discomfort and/or symptoms associated with episodic heartburn. When commercially available antacids are selected for use in accordance with the present invention, such as Maalox-Plus ®, Mylanta ®, Tums ®, Gelusil ®, etc., it is preferable to use the high potency, flavored (mint, cherry, lemon, etc.) liquid antacids, such as, for example, Maalox-Plus ® and Mylanta-II ®.

By the term "substantially together," it is meant herein that when the active ingredients, i.e., an antacid and a histamine $H_2$-receptor antagonist, are taken in separate dosage forms, they can be consumed either simultaneously or within a period of time such that the immediate, temporary and sustained relief obtained is constant and uninterrupted. For example, the active ingredients may be taken together or within a few seconds to a few minutes of one another. Nevertheless, it is preferable to ingest a single unitary dose which includes both active ingredients and is in liquid form.

Typical dosages include about 30 mls or 2 tablespoons of a high-potency antacid having an acid-neutralizing capacity equal to the present formulations of, for example, Maalox Plus ®, Mylanta-II ®. With respect to the histamine $H_2$-receptor antagonist, the amount included in the single dosages is believed to be about 200 mg to about 300 mg of cimetidine or about 100 mg to about 150 mg of ranitidine. For example, a typical dosage amount for providing immediate and sustained relief from episodic heartburn in an adult is about 30 mls of a high potency flavored antacid or the equivalent thereof and about 200 mg to about 300 mg of cimetidine or 100 mg to about 150 mg of ranitidine administered between about one and about four times per day. Notwithstanding, it should be appreciated that the oral medications of the instant invention are to be taken on an as-needed basis whenever pain or symptoms associated with episodic heartburn is experienced.

Antiflatulents may also be used in combination with the antacids and histamine $H_2$-receptor antagonists in the present invention and include those antiflatulents which are conventionally used in the treatment of gastrointestinal dysfunction, such as, for example, simethicone. Antiflatulents may be used in the present invention in dosage amounts conventionally used in the treatment of gastrointestinal dysfunction.

The pharmaceutical compositions may be in a form suitable for oral use, for example, as tablets, lozenges, aqueous or oily suspensions, dispersible powders or granules, emulsions, hard or soft capsules, syrups or elixirs. Compositions intended for oral use may be prepared according to any method known to the art for the manufacturer of pharmaceutical compositions and such compositions may contain one or more agents such as, for example, sweetening agents, flavoring agents, coloring agents and the like, in order to provide a pharmaceutically elegant and palatable preparation. Tablets contain the active ingredient in admixture with nontoxic pharmaceutically acceptable excipients which are suitable for manufacture of tablets. These excipients may be, inert diluents, for example, calcium carbonate, sodium carbonate, lactose, calcium phosphate or sodium phosphate; granulating and disintegrating agents, for example, maize starch, or alginic acid; binding agents, for example, starch, gelatine or acacia, and lubricating agents, for example, magnesium stearate or stearic acid. The tablets may be uncoated or they may be coated by known techniques to delay disintegration and absorption in the gastrointestinal tract and thereby provide an even longer sustained action over a period of time.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with a suitable oil medium, for example, arachis oil, liquid paraffin or olive oil.

Aqueous suspensions contain the active ingredients in admixture with excipients suitable for the manufacture of aqueous suspensions. Such excipients may be suitable suspending agents, for example, sodium carboxymethyl cellulose, methyl cellulose, hydroxy propyl methyl cellulose, sodium alginate, polyvinylpyrrolidone, gum tragacanth and gum acacia; dispersing or wetting agents may be any suitable naturally occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol, for example, polyoxyethylene sorbitol monnoleate, or condensation product of ethylene oxide with partial esters derived from fatty acids and hexitol and anhydrides, for example, polyoxyethelyne sobirtan monooleate. The aqueous suspensions may also contain one or more suitable preservatives, for example, ethyl, or n-propyl, p-hydroxy benzoate, one or more suitable coloring agents, one or more suitable flavoring agents and one or more suitable sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and on or more preservatives. Suitable dispersing or wetting agents and suspending agents may be exemplified by those already mentioned above. Additional suitable excipients, for example, sweetening, flavoring and coloring agents, may also be present.

Syrups and elixirs may be formulated with suitable sweetening agents, for example, glycerol, sorbitol, or sucrose. Such formulations may also contain suitable demulcents, preservatives and flavoring and coloring agents.

In order to further illustrate the present invention and the advantages thereof, the following specific Examples are given, it being understood that these Examples are intended only to be illustrations without serving as a limitation on the scope of the present invention.

EXAMPLE I

A 49-year old man diagnosed with episodic heartburn relating to dietary indiscretion was treated with a histamine $H_2$-receptor antagonist. He reported that, while the histamine $H_2$-receptor antagonist produced symptom relief, he did not experience relief until some time after he ingested the medication.

This man was then treated with 400 mg of cimetidine (tablet), 30 mls of Maalox Plus ® (liquid), or both. He reported that the Maalox-Plus ® produced symptomatic relief, but that a second dose was necessary after one-half hour. He also reported that the cimetidine relieved the heartburn, but only after about 45 to 60 minutes. He reported, however, that the combination of both Maalox-Plus ® and cimetidine produced immediate (within 5 minutes) as well as temporary and sustained relief. He further reported that there was no decrease in the length of time in which relief was obtained when both were taken together.

EXAMPLE II

A 41-year old man diagnosed with episodic heartburn relating to dietary indiscretion was treated with 30 mls of Maalox-Plus ® (liquid), 300 mg of cimetidine (liquid), or both. He reported that symptom relief was superior with the combination, when compared to using each individual agent alone. More particularly, he reported that when the Maalox-Plus ® was used alone, he obtained immediate, but only temporary, relief, and that when cimetidine was used alone, he reported relief of heartburn after 45-60 minutes. However, when he used them together, he reported immediate, temporary and sustained relief from heartburn following ingestion.

EXAMPLE III

A 33-year old man diagnosed with episodic heartburn relating to dietary indiscretion was treated with 30 mls of Maalox Plus ® (liquid), 150 mg of ranitidine (tablet), or both. He reported that symptom relief was superior with a combination, when compared to using each individual agent alone. More particularly, he reported that when the Maalox-Plus ® was used alone, he obtained only partial relief within about 10 minutes after ingestion, which lasted only about 30 minutes, and that when ranitidine was used alone, he reported complete relief that began approximately about 60 minutes after ingestion and lasted about 8 hours. However, when he used them in combination, he reported partial relief within about 10 minutes, but complete relief within about 45 minutes, lasting about 8 hours after ingestion.

EXAMPLE IV

A 21-year old man diagnosed with episodic heartburn relating to dietary indiscretion was treated with Tums ® tablets, 150 mg of ranitidine (tablet), or both. He reported that symptom relief was superior with a combination, when compared to using each individual agent alone. More particularly, he reported that when the Tums ® were used alone, he obtained relief within about five minutes after ingestion, for about one hour, and that when ranitidine was used alone, he reported complete relief after 45 minutes, which lasted indefinitely. However, when he used them in combination, he reported immediate, temporary and sustained relief following ingestion.

EXAMPLE V

A 31-year old man diagnosed with episodic heartburn relating to dietary indiscretion was treated with 30 mls of Mylanta II ® (liquid), 400 mg of cimetidine (tablet), or both. He reported that symptom relief was superior with a combination, when compared to using each individual agent alone. More particularly, he reported that when the Mylanta II ® was used alone, he had relief of heartburn within 3-5 minutes after ingestion, and that when cimetidine was used alone, he reported complete and sustained relief after 30-40 minutes following ingestion. However, when he used them in combination, he reported immediate, temporary and sustained relief following ingestion.

EXAMPLE VI

A 50-year old woman diagnosed with episodic heartburn relating to dietary indiscretion was treated with 30 mls of Maalox Plus ® (liquid), 400 mg of cimetidine (tablet), or both. She reported that symptom relief was superior with a combination, when compared to using each individual agent alone. More particularly, she reported that when the Maalox-Plus ® was used alone, she obtained only partial immediate relief lasting 60 minutes, and that when cimetidine was used alone, she reported complete and sustained relief within 30-40 minutes. However, when he used them in combination, she reported partial relief within 5-10 minutes and complete sustained relief within 30 minutes following ingestion.

EXAMPLE VII

A 32-year old man with alleged episodic heartburn related to dietary indiscretion was treated with 30 mls of Mylanta II ® (liquid), 400 mg of cimetidine (tablet), or both. He reported no relief of symptoms with any of the regimens examined. Upon further questioning of the man and diagnosis, it was determined that his symptoms were actually associated with abdominal bloating and flatulence, not episodic heartburn.

The present invention may, of course, be carried out in other specific ways than those herein set forth without departing from the spirit and essential characteristics of the invention. The present embodiments are, therefore, to be considered in all respects as illustrative and not restrictive and any changes coming within the meaning and equivalency range of the appended claims are to be embraced therein.

Having described my invention, I claim:

1. A method of providing immediate and sustained relief from pain, discomfort and/or symptoms associated with episodic heartburn in a human, said method comprising:
orally administering to a human together or substantially together an antacid in an amount effective to substantially neutralize gastric acid and a histamine $H_2$-receptor antagonist in an amount effective to substantially inhibit or block gastric acid secretion for providing the human with immediate and sustained relief from pain, discomfort and/or symptoms associated with episodic heartburn, the immediate and sustained relief provided lasting longer in duration than when the human is orally treated with only the antacid and the immediate and sustained relief provided being faster than and lasting at least about as long in duration as when the human is orally treated with only the histamine $H_2$-receptor antagonist.

2. A method of claim 1, the histamine $H_2$-receptor antagonist being cimetidine.

3. A method of claim 1, the histamine $H_2$-receptor antagonist being ranitidine.

4. A method of claim 1, the histamine $H_2$-receptor antagonist being selected from a group consisting of famotidine and nizatidine.

5. A method of claim 1, the antacid being selected from a group consisting of aluminum hydroxide, calcium carbonate, magnesium hydroxide, sodium bicarbonate and mixtures thereof.

6. A method of claim 1, the antacid being a high potency antacid.

7. A method of claim 1, the antacid being a flavored antacid.

8. A method of claim 2, the cimetidine being administered in a daily dosage amount of between about 200 mg and about 1200 mg.

9. A method of claim 3, the ranitidine being administered in a daily dosage amount of between about 100 mg and about 450 mg.

10. A method of claim 1, said method including the further step of administering an effective gas inhibiting amount of an antiflatulent.

11. A method of claim 10, the antiflatulent being simethicone.

12. A method of claim 1, the antacid and the histamine $H_2$-receptor antagonist being administered in a dosage form selected from a group consisting of liquid and solid dosage forms and mixtures thereof.

13. An oral pharmaceutical medication for providing immediate and sustained relief from pain, discomfort and/or symptoms associated with episodic heartburn in a human, said oral pharmaceutical medication consisting essentially of:
an antacid in an amount effective to substantially neutralize gastric acid;
a histamine $H_2$-receptor antagonist in an amount effective to substantially inhibit or block gastric acid secretion; and
a pharmaceutically acceptable carrier;
said oral pharmaceutical medication providing immediate and sustained relief from pain, discomfort and/or symptoms associated with episodic heartburn in the human, said immediate and sustained relief lasting longer in duration than when the human is orally treated with only the antacid and being faster than and lasting at least about as long in duration as when the human is orally treated with only the histamine $H_2$-receptor antagonist.

14. A pharmaceutical medication of claim 13, said oral pharmaceutical medication being in a liquid dosage form.

15. A pharmaceutical medication of claim 13, said oral pharmaceutical medication being in a solid dosage form.

16. A pharmaceutical medication of claim 13, said histamine $H_2$-receptor antagonist being cimetidine.

17. A pharmaceutical medication of claim 16, said cimetidine being present in an amount of between about 200 mg and about 300 mg.

18. A pharmaceutical medication of claim 13, said histamine $H_2$-receptor antagonist being ranitidine.

19. A pharmaceutical medication of claim 18, said ranitidine being present in an amount of between about 100 mg and about 150 mg.

20. A pharmaceutical medication of claim 13, said histamine $H_2$-receptor antagonist being selected from a group consisting of famotidine and nizatidine.

21. A pharmaceutical medication of claim 13, said antacid being selected from a group consisting of aluminum hydroxide, calcium carbonate, magnesium hydroxide, sodium bicarbonate and mixtures thereof.

22. A pharmaceutical medication of claim 13, said antacid being a flavored antacid.

23. A pharmaceutical medication of claim 13, said antacid being a high potency antacid.

24. A pharmaceutical medication of claim 13, said oral medication further including an effective amount of an antiflatulent.

25. A pharmaceutical medication of claim 24, said antiflatulent being simethicone.

26. A pharmaceutical medication of claim 13, said antacid being aluminum hydroxide and magnesium hydroxide, and said histamine $H_2$-receptor antagonist being cimetidine.

27. A pharmaceutical medication of claim 13, said antacid being aluminum hydroxide and magnesium hydroxide, and said histamine $H_2$-receptor antagonist being ranitidine.

* * * * *